United States Patent [19]

Kraus

[11] 4,346,039

[45] Aug. 24, 1982

[54] SYNTHESIS OF OCHRATOXINS

[75] Inventor: George A. Kraus, Ames, Iowa

[73] Assignee: Iowa State University Research Foundation, Inc., Ames, Iowa

[21] Appl. No.: 245,382

[22] Filed: Mar. 19, 1981

[51] Int. Cl.$^3$ .............................................. C07D 311/76
[52] U.S. Cl. ....................................... 549/289; 560/67
[58] Field of Search ...................... 260/343.44, 343.45; 560/67

[56] References Cited

PUBLICATIONS

Kraus, Chem. Abst., 94:47077m.
Steyn et al., Tetrahedron, vol. 23, pp. 4449–4461, 1967.
Roberts et al., J. Chem. Soc., (C), 1970, p. 278.

*Primary Examiner*—Jane T. Fan

*Attorney, Agent, or Firm*—Zarley, McKee, Thomte, Voorhees & Sease

[57] ABSTRACT

A simple, direct synthesis route is provided for Ochratoxin compounds, particularly Ochratoxin A, Ochratoxin B, and Ochratoxin C. The reaction involves treating the dimethyl ester of 2-hydroxy-4-methylbenzene-1,3-dioic acid with a deprotonating agent, followed by addition of acetaldehyde, to provide a precursor compound, which can conveniently be converted to Ochratoxins A, B or C. The synthesis route allows for the first time laboratory and industrial scale synthesis of ochratoxins A, B and C in large quantities and pure form making them available as toxins, for use as antitoxin investigation works, and for biological activity investigations and residue studies.

10 Claims, No Drawings

SYNTHESIS OF OCHRATOXINS

GRANT REFERENCE

The invention described herein was made in the course of work under a grant from the National Institutes of Health, No. DM 24474.

BACKGROUND OF THE INVENTION

Ochratoxins are known compounds. They are toxic metabolites known to be produced from some strains of the fungus *Aspergillus ochraceus.* Interest in the ochratoxins, and particularly ochratoxins A, B and C, is prompted by the health hazard they pose because of their occurrence in agricultural products such as silage, hay, feedstuffs and corn. That is to say, the spores of the *Aspergillus ochraceus* fungus are present in these materials; and, if the right fermenting moisture and temperature conditions occur the resulting metabolism decomposition products include the ochratoxins. Thus, they may occur in nature, in foodstuffs which enter the food chain ultimately leading to man. It is known that the ochratoxins may cause kidney lesions, ultimately leading, in acute cases, to renal failure.

However, because there never has been a practical synthesis route for the ochratoxins, it has been difficult to isolate and study them in the laboratory. Such studies are desirable for determining the precise effects of each ochratoxin compound, for determining possible anti-toxins, and for determining the residue effect on the food chain.

While some ochratoxins may be obtained in small microgram quantities from the fermentation of *Aspergillus ochraceus*, it is difficult to obtain the pure compounds. Thus one never knows for sure, in controlled studies using fermentation extract, whether it is in fact the effect of the ochratoxins which is being studied. Moreover, the sparing availability of the pure compounds has made it virtually impossible for any meaningful anti-toxin studies, or residue studies.

There have in the past been previously reported literature routes for the synthesis of some Ochratoxins; see, for example: Steyn, P. S.; Holzapfel, C. W., *Tetrahedron*, 1967, 23, 4449; and Roberts, J. C.; Woollven, P. *J. Chem. Soc. C.*, 1970, 278. However, these are not practical, involve a multitude of lengthy, complex steps and some very expensive chemicals, such as silver compounds.

Thus, it can be seen that there is a real and continuing need for a simple, direct and inexpensive synthesis route for Ochratoxins. The availability of the pure compounds in quantity would allow for toxin and anti-toxin studies, biological activity testing, and residue studies.

The primary object of this invention is to fulfill this continuing need.

The method and manner of accomplishing this primary objective, as well as others, will become apparent from the detailed description of the invention which follows.

SUMMARY OF THE INVENTION

Ochratoxin precursor compounds having the building block nucleus for ready conversion into Ochratoxins A, B and C, are prepared by reacting the dimethyl ester of 2-hydroxy-4-methylbenzene-1,3-dioic acid with a deprotonating agent, preferably di-isopropyl-amide, followed by addition of acetaldehyde as an electrophilic agent, to provide the lactone methyl-1,4-dihydro-8-hydroxy-3-methyl-1-H-2 benzopyran-1-one-7-carboxylate. This lactone may be chlorinated, hydrolyzed and condensed with L-phenylalanine t-butyl ester to provide Ochratoxin A; or, the chlorination step may be omitted to provide Ochratoxin B; or, the Ochratoxin A may itself be reacted to form its ethyl ester, which is Ochratoxin C.

DETAILED DESCRIPTION OF THE INVENTION

These Ochratoxins have the formula:

[Structure: PhCH$_2$—CH(CO$_2$H)—NC(=O)— attached to a benzene ring bearing OH, with fused ring containing O, C=O, and CH$_3$; X substituent on ring]

Ochratoxin A:
X = Cl

Ochratoxin B:
X = H

Ochratoxin C:
CO$_2$H replaced with CO$_2$C$_2$H$_5$

As earlier stated, if the carboxylic acid group of Ochratoxin A is replaced in a simple esterification reaction with ethyl alcohol, the resulting compound is Ochratoxin C.

The starting material for the present reaction is the dimethyl ester of 2-hydroxy-4 methylbenzene 1,3-dioic acid of the formula:

[Structure: benzene ring with OH, two CO$_2$CH$_3$ groups, and CH$_3$]

Compound 3

This starting material is a known product and may be simply and conveniently prepared in one step from dimethyl-3-oxopentane dicarboxylate and the sodium salt of hydroxymethyleneacetone. The reaction forming the starting material is fully disclosed in the following article: Prelog, V.; Metzler, O; Jesen, O. *Helv. Chim. Acta*, 1947, 30, 675, which is incoporated herein by reference. Since this first step preparation of starting material (Compound 3) is known and does not form a part of part of the applicant's invention, it will only briefly be described, and later illustrated in the examples. Briefly, the dimethyl 3-oxo pentane dicarboxylate and hydroxymethyleneacetone are mixed in the presence of sodium hydroxide, at room temperature, under conditions which exclude air, i.e., flushing of nitrogen. The reaction is run in ethyl alcohol at room temperature for about 12 hours, after which the solvent is removed, an aqueous acid solution is added, followed by ether extraction to provide compound 3, as shown above.

By way of a visual summary of the reaction route of the present invention, the sequence is shown in the following reaction scheme.

3 $\xrightarrow{\text{2iPr}_2\text{NLi, THF}}_{\text{CH}_3\text{CHO}}$ (Compound 4)

$\xrightarrow[\text{CH}_3\text{OH}><]{\text{(1)SO}_2\text{Cl}_2, \text{CH}_2\text{Cl}_2}_{\text{LiOH.H}_2}$ (Compound 5)

Compound 3 is reacted with a deprotonating agent followed by addition of acetaldehyde electrophilic agent to provide methyl-1,4-dihydro-8-hydroxy-3-methyl 1-H-2 benzopyran-1-one-7-carboxylate, hereinafter, compound (4). This reaction is a deprotonating reaction and is conducted in the presence of a deprotonating agent of the general formula: $R_1 R_2 NM$. Such deprotonating agents are, of course, known. "$R_1$" and "$R_2$" may be straight or branched chain alkyl groups with the alkyl group being $C_2$ or greater, preferably $C_2$ to $C_4$. Most commonly "$R_1$" and "$R_2$" are isopropyl. "M" represents a metal ion and may be lithium, sodium, potassium or magnesium. Most preferably "M" is lithium and the deprotonating agent is lithium diisopropylamide. The amount of acetaldehyde electrophile used should be at least an equivalent amount, preferably an excess.

This first reaction is conducted in the presence of an inert solvent which will not react with the deprotonating agent. Typical of such solvents are tetrahydrofuran (THF), ether and glyme.

The reaction temperature does not appear to be critical and it may be run at temperatures as low as $-78°$ C. up to $0°$ C.

Time of the reaction is not critical. In the reaction sequence, the deprotonation step, that is the proton removal to make the anion portion, is allowed to continue preferably from about five minutes to about 30 minutes; and, thereafter, the acetaldehyde electrophile is added. Here again, time does not appear to be critical, since the reactions may well be instantaneous but the time limits expressed will assure completion of the reaction.

After the lactone (4) has been synthesized, it is isolated in a conventional workup manner, as illustrated in the examples. That is, acetic acid is added to neutralize, and ether and water are added to dilute the solution and it separates into layers. The lactone (4) is in the ether layer. The aqueous layer is once again ether extracted, and this extract added to the prior ether extract to assure as complete a recovery as possible of lactone (4). The ether layer is then dried with sodium sulfate and the ether evaporated to provide the solid lactone (4).

As can be seen from the deprotonation reaction, the proton of the hydroxyl group is removed as well as the proton of the methyl group to allow reaction with the acetaldehyde to form the lactone ring.

It is the lactone (4) which forms the basic building block for the synthesis of Ochratoxins A, B and C. The exact synthesis route after preparation of lactone (4) depends upon whether one is desirous of forming Ochratoxin A, Ochratoxin B, or Ochratoxin C. If one desires to form Ochratoxin A, since it contains a halogen moiety, the next step will be a chlorination reaction to provide compound (5).

In the chlorination reaction, the lactone (4) is dissolved in a chlorocarbon solvent which may, for example, be carbon tetrachloride, chloroform, or methylene chloride, preferably methylene chloride. A chlorinating agent is added such as sufuryl chloride, or molecular chloride, which could be bubbled through the methylene chloride. Such a chlorination reaction is typically conducted under neutral conditions. In this synthesis, the chlorination reaction is followed by an ester hydrolysis reaction in the presence of lithium hydroxide and a solvent such as methanol.

As can be seen from the general reaction scheme depicted, it is a straightforward, simple replacement reaction. As further seen in the examples, the reaction is preferably conducted in the presence of an excess amount of chlorinating agent, with the generated hydrochloric acid removed by vacuum stripping. Excess solvent is removed by distillation leaving compound (5). The methanol-lithium hydroxide serves to convert the ester group to a carboxylic acid group in a classic ester hydrolysis reaction. It can be conducted in the same reaction vessel as the chlorination reaction by a sequence of first chlorinating, followed by the ester hydrolysis reaction.

The chlorination reaction can be run at room temperature, with pressure not being a factor. In laboratory experiments, times of from about ten hours to about 20 hours have been employed. The sequential esterification reaction is conducted under reflux conditions at the boiling point of the solvent, methanol. It is also preferably conducted under a nitrogen blanket, and may be run for from ten hours to 20 hours.

With regard to the chlorinating reaction, it is preferred to employ an excess of the agent, such as sulfuryl chloride. It has been found that an excess is needed. Desirable results are obtained when at least three times the required stoichiometric amount is employed. Also, as is tradition in the ester hydrolysis, an excess of hydrolyzing agent is also employed, at times even as high as a tenfold excess.

Compound (5) is isolated in a traditional workup. Methanol is removed by vacuum, hydrochloric acid is added to acidify, an ether extraction follows, leaving, after ether evaporation, a residue compound (5).

An examination of the basic formula for the Ochratoxins shown previously reveals that compound (5) contains the basic skeletal structure, requiring only a condensing reaction between L-phenylalanine t-butyl ester and compound (5) to yield Ochratoxin A. This condensation reaction is a known reaction, see Roberts et al. *Journal Chem. Soc.* (C), 1970 at 278, which has previously been incorporated herein by reference.

Basically the procedure for converting compound (5) to Ochratoxin A is an addition reaction between compound (5) and L-phenylalanine t-butyl ester. To help condense the ester with compound (5), an appropriate and known condensing agent is employed, for example, 2-ethoxy-1-ethoxycarbonyl-1,2-dihydroquinoline (EEDQ). For further details of this known reaction see the example and the incorporated reference. The resulting compound is Ochratoxin A. If the chlorination step is omitted, the resulting compound is Ochratoxin B. And, finally, if the Ochratoxin A is reacted with ethyl alcohol to form the corresponding ester on the carboxylic acid moiety of Ochratoxin A, the resulting compound will be Ochratoxin C.

In many instances the resulting yield far exceeds that of those reported in the literature. In particular, in many runs, the overall yield from the commercially available starting materials to the final Ochratoxin product exceeds 20%, indicating this route is by far the most efficient preparation of Ochratoxin intermediates.

The following example serves to illustrate, but not limit, the process of the present invention.

In the following example, tetrahydrofuran (THF) was distilled from lithium aluminum hydride. Melting points were determined on a Fisher-Johns melting point apparatus and are uncorrected. Nuclear magnetic resonance spectra were determined on the Hitachi Perkin-Elmer R20B. The $^{13}C$ NMR spectrum was determined on a Joelco FX-90 Q.

EXAMPLE

Compound (3), that is the dimethyl ester of 2-hydroxy-4-methyl-benzene-1,3-dioic acid was utilized to prepare compound (4), that is Methyl-1,4-dihydro-8-hydroxy-3-methyl-1H-2-benzopyran-1-one-7-carboxylate in the following manner. To a solution of 14.9 mmoles of lithium-diisopropyl-amide deprotonating agent prepared from 2.4 M n-butyl lithium (6.2 mL, 14.9 mmoles) and diisopropylamine (2.24 mL, 16 mmoles) in 10 mL THF at $-78°$ C. was added diester 3 (1.54 g, 6.9 mmoles) in 3 mL THF over 3 min. After the deep red solution was stirred 10 minutes, neat acetaldehyde (1.2 mL, 21.5 mmoles) was added and the solution was stirred 5 minutes at $-78°$ C. and 15 minutes at $0°$ C. The reaction was quenched at $0°$ C. with acetic acid (1.99 g) and diluted with ether and water. The aqueous layer was extracted twice with ether. The combined organic layers were dried over sodium sulfate, concentrated in vacuo and chromatographed on silica gel to afford 1.13 g yellow solid. The solid had a melting point of $108°-110°$ C. NMR(CDCl$_3$); $\delta 1.53$ (d, 3H, J=6 Hz), 2.6–3.2(m, 2H), 3.93(s,3H), 4.4–4.8(m, 1H); 6.72(d, 1H, J=9 Hz), 8.03(d, 1H, J=9 Hz).

Compound (4) was converted to 5-chloro-1,4-dihydro-8-hydroxy-3-methyl-1H-2-benzopyran-1-one-7-carboxylic acid, that is compound 5 in the following manner. To a solution of 4 (0.361 g, 1.53 mmol) in 3 mL methylene chloride at ambient temperature was added sulfuryl chloride chlorinating agent (0.50 mL, 5.18 mmol). The solution was stirred under nitrogen atmosphere 20 hr, concentrated in vacuo and suspended in 5 mL methanol. Lithium hydroxide monohydrate (0.700 g, 16.6 mmol) was added to the suspension and the suspension was heated to reflux under a nitrogen atmosphere 20 hours in order to effect an ester hydrolysis. After the solution had cooled, most of the methanol was removed in vacuo. The semisolid was dissolved in water, extracted once with ether and the aqueous layer was then acidified to pH 2 with 3 N HCl. The solution was extracted twice over sodium sulfate, concentrated in vacuo and recrystallized from acetone-methanol to afford 0.189 g of a white solid with a melting point of $246°$ C. (compound 5). NMR(D6-DMSO) $\delta 1.5$(d, 3H, J=6 Hz), 2.6–3.2(m, 2H), 4.3–4.8(m, 1H), 8.0(s, 1H). CMR(D6-DMSO) 20.00, 32.08, 74.23, 112.31, 117.73, 120.44, 135.88, 143.08, 160.31, 165.24, 167.03.

Compound (5) may be converted to Ochratoxin A by conventional procedures involving condensation with L-phenylalanine tertiary butyl ester in the presence of a condensing agent as described in the previously incorporated 1970 Journal of Chemical Society article. In particular, compound (5) is dissolved in tetrahydrofuran (20 ml.) and L-(−)-phenylalanine t-butyl ester (22 mg) and 2-ethoxy-1-ethoxycarbonyl-1,2-dihydroquinoline (EEDQ) (25 mg) is then added. The solution is stirred at room temperature for 15 hours, filtered, and evaporated in vacuo at room temperature. The residue is dissolved in glacial acetic acid (0–5 ml.) and the solution is cooled to $10°$. A cooled solution of 45% hydrogen bromide in acetic acid is then added and the mixture is shaken at this temperature for five minutes. Cold ethyl acetate (100 ml) is added and the resulting solution is washed with cold sodium acetate solution (until the pH of the washings was >4) and then with water (2×20 ml.) The solution is dried (MgSO$_4$) and is evaporated in vacuo at room temperature to give a colorless glass which is dissolved in benzene at $30°$. (Since it has been reported that solutions of Ochratoxin A, when overheated, give rise to insoluble material, care was taken to keep temperatures below $35°$). The solution is filtered and most of the solvent is removed at $30°$ in a stream of nitrogen. Sometimes unsolvated (−,±)-Ochratoxin A crystallized spontaneously as colorless prisms. This last procedure, that is the conversion of compound (5) to Ochratoxin A, is the identical procedure reported in the previously incorporated Roberts et al. Journal article.

Ochratoxin A is converted to (C) by esterification with ethyl alcohol. Ochratoxin B is prepared by the exact procedure as A, with omission of the chlorination step.

It can therefore be seen that an economical, good yield, minimum step synthesis is used to prepare, not only precursors for Ochratoxin, but also Ochratoxin A, Ochratoxin B and Ochratoxin C.

What is claimed is:

1. A method of synthesis of an Ochratoxin precursor compound, comprising:
reacting the dimethyl ester of 2-hydroxy-4-methyl-benzene-1,3 dioic acid with a deprotonating agent of the formula: $R_1R_2NM$, with $R_1$ and $R_2$ being straight or branched chain alkyl group of $C_2$ or greater chain length, and M being a metal selected from the group of lithium, sodium, potassium and magnesium, followed by addition of acetadehyde to provide methyl-1,4-dihydro-8-hydroxy-3-methyl-1-H-2-benzopyran-1-one-7-carboxylate.

2. The method of claim 1 wherein the reaction is conducted in the presence of an inert solvent.

3. The method of claim 2 wherein the solvent is selected from the group of THF, ether and glyme.

4. The method of claim 3 wherein the reaction temperature is from about $0°$ to about $-78°$ C.

5. The method of claim 1 wherein the deprotonating agent is lithium diisopropylamide.

6. The method of claim 5 wherein said methyl-1,4-dihydro-8-hydroxy-3-methyl-1-H-2-benzopyran-1-one-7-carboxylate is reacted with a chlorinating agent.

7. The method of claim 6 wherein as a final step to provide Ochratoxin A the chlorinated compound is reacted with L-phenylalanine t-butyl ester.

8. The process of claim 5 wherein said methyl-1,4-dihydro-8-hydroxy-3-methyl-1-H-2-benzopyran-1-one-7-carboxylate, is reacted with L-phenylanine t-butyl ester in the presence of a condensing agent to provide Ochratoxin B.

9. The method of claim 6 wherein Ochratoxin A is reacted in a straightforward ester reaction with ethyl alcohol to provide the ethyl ester of Ochratoxin A.

10. A method of synthesis of Ochratoxin A comprising: reacting dimethyl-3-oxo-pentane-dicarboxylate with sodium hydroxymethyleneacetone to provide the dimethyl ester of 2-hydroxy-4-methylbenzene-1,3-dioic acid;

reacting said dimethyl ester of 2-hydroxy-4-methylbenzene-1,3-dioic acid with a deprotonating agent of the formula: $R_1 R_2 NM$ with "$R_1$" and "$R_2$" being straight or branched chain alkyl groups of $C_2$ or greater chain length, and "M" being a metal selected from the group consisting of lithium, sodium, potassium, or magnesium, followed by addition of acetaldehyde as an electrophile, to provide methyl-1,4-dihydro-8-hydroxy-3-methyl-1-H-2-benzopyran-1-one-7-carboxylate, a lactone;

chlorinating said lactone to provide an Ochratoxin precursor of 5-chloro-1,4-dihydro-8-hydroxy-3-methyl-1-H-2-benzopyran-1-one-7-carboxylic acid;

and thereafter reacting the said Ochratoxin precursor with L-phenylalanine-t-butyl ester in the presence of a condensing agent, to provide Ochratoxin A.

* * * * *